US008420137B2

(12) United States Patent
Wenk et al.

(10) Patent No.: US 8,420,137 B2
(45) Date of Patent: Apr. 16, 2013

(54) BIOACTIVE COMPOSITION FOR COSMETIC APPLICATIONS

(75) Inventors: Hans Henning Wenk, Mulheim a. d. Ruhr (DE); Mike Farwick, Essen (DE); Stefan Bergfried, Essen (DE); Ursula Maczkiewitz, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 0 days.

(21) Appl. No.: 13/106,532

(22) Filed: May 12, 2011

(65) Prior Publication Data

US 2011/0217400 A1    Sep. 8, 2011

Related U.S. Application Data

(62) Division of application No. 12/249,250, filed on Oct. 10, 2008, now abandoned.

(30) Foreign Application Priority Data

Oct. 17, 2007  (DE) .......................... 10 2007 049 612

(51) Int. Cl.
*A61K 36/906*  (2006.01)
*A61K 36/00*   (2006.01)

(52) U.S. Cl.
USPC .......................................... 424/756; 424/773

(58) Field of Classification Search .................. None
See application file for complete search history.

(56) References Cited

U.S. PATENT DOCUMENTS

| | | | | |
|---|---|---|---|---|
| 5,175,358 A * | 12/1992 | Capai et al. | ................... | 562/537 |
| 5,861,415 A | 1/1999 | Majeed et al. | | |
| 6,046,191 A * | 4/2000 | Hamley et al. | ............. | 514/232.8 |
| 6,344,575 B1 * | 2/2002 | Rubin | .............................. | 554/23 |
| 2006/0275238 A1 | 12/2006 | Blasko-Begoihn et al. | | |
| 2006/0275239 A1 | 12/2006 | Farwick et al. | | |
| 2007/0003509 A1 | 1/2007 | Farwick et al. | | |
| 2008/0108709 A1 | 5/2008 | Meyer et al. | | |
| 2008/0145320 A1 | 6/2008 | Wenk et al. | | |
| 2008/0200400 A1 | 8/2008 | Lersch et al. | | |
| 2008/0249073 A1 | 10/2008 | Farwick et al. | | |
| 2008/0260675 A1 | 10/2008 | Farwick et al. | | |
| 2009/0054521 A1 | 2/2009 | Herrwerth et al. | | |
| 2009/0105110 A1 | 4/2009 | Wenk et al. | | |

FOREIGN PATENT DOCUMENTS

| | | |
|---|---|---|
| CN | 1319418 A | 10/2001 |
| DE | 1 165 574 | 8/1960 |
| DE | 37 40 186 A1 | 1/1989 |
| DE | 39 38 140 A1 | 8/1991 |
| DE | 40 09 347 A1 | 9/1991 |
| DE | 42 38 081 A1 | 7/1993 |
| DE | 42 04 321 A1 | 8/1993 |
| DE | 42 29 707 A1 | 3/1994 |
| DE | 42 29 737 A1 | 3/1994 |
| DE | 43 09 372 A1 | 9/1994 |
| DE | 43 24 219 A1 | 1/1995 |
| DE | 198 55 934 A1 | 6/2000 |
| EP | 0 666 732 B1 | 8/1995 |
| JP | 2004269489 | 9/2004 |
| KR | 2002081003 * | 10/2002 |
| WO | WO2007109210 A2 | 9/2007 |

OTHER PUBLICATIONS

Carolina et al. Extraction of Essential Oil and Pigments From *Curcuma longa* [L.] by Steam Distillation and Extraction With Volatile Solvents. Journal of Agric. Food Chem. 2003, 51, 6802-6807.*
Apisariyakul et al. Antifungal activity of turmeric oil extracted from *Curcuma longa* (Zingiberaceae). Journal of Ethnopharmacology. 49. 1995. 163-169.*
Kim, Jae K. et al., "Color Improvement by Irradiation of *Curcuma aromatica* Extract for Industrial Application" Radiation Physics and Chemistry (2006) pp. 449-452, vol. 75.
Voeste, T. et al., Ullmann's Encyclopedia of Industrial Chemistry (Release 2006) 7th Edition in the chapter "Liquid-Solid Extraction".
Finkel, P., "Formulierun Kosmetischer Sonnenschutzmittel" SÖFW—Journal (1996) pp. 543-548, vol. 122.
Gösele, W. et al., Ullmann's Encyclopedia of Industrial Chemistry (Release 2006) 7th Edition in the chapter "Filtration".
Jayaprakasha, G.K. et al., "Improved HPLC Method for the Determination of Curcumin, Demethoxycurcumin, and Bisdemethoxycurcumin" Journal of Agricultural and Food Chemistry (2002) pp. 3668-3672, vol. 50(13).
"Antioxidant Activity of Curcumin and Related Compounds" Biological Pharmacology (1976) pp. 1811-1812, vol. 23.
Negi, P.S. et al., "Antibacterial Activity of Turmeric Oil: A Byproduct from Curcumin Manufacture" Journal of Agricultural and Food Chemistry (1999) pp. 4297-4300, vol. 47(10).
Apisariyakul, A. et al., "Antifungal Activity of Turmeric Oil Extracted from *Curcuma longa* (Zingiberaceae)" Journal of Ethno Pharmacology (1995) pp. 163-169, vol. 49.
Ruby, A.J. et al., "Anti-Tumour and Antioxidant Activity of Natural Curcuminoids" Cancer Letters (1995) pp. 79-83, vol. 94.
Sousamini, K.K. and Kuttan, R., "Cytotoxic and Tumor Reducing Properites of Curcumin" Indian Journal of Pharmacology (1988) pp. 95-101, vol. 20.
Jayaprakasha, G. K. et al., "Chemical composition of turmeric oil—A byproduct from turmeric oleoresin industry and its inhibitory activity against different fungi", Zeitschrift Fuer Naturforschung, Section C, Biosciences, Bd. 56, Nr. 1-2, Jan. 1, 2001, Seiten 40-44, XP009143757, ISSN: 0341-0382.

(Continued)

*Primary Examiner* — Christopher R. Tate
(74) *Attorney, Agent, or Firm* — Scully, Scott, Murphy & Presser, P.C.

(57) ABSTRACT

The invention relates to a process for the preparation of a plant extract from *Curcuma* plants, characterized by the process steps process step A) liquid extraction of *Curcuma* rhizomes, process step B) optionally, separation of a curcuminoid-containing solid obtained by precipitation from the extraction mixture obtained in process step A), process step C) removal of solvents present from the extraction mixture obtained in process step A) or B) to obtain a concentrate and process step D) distillation of the concentrate at a pressure of less than 1 bar to give the extract as distillate.

12 Claims, 4 Drawing Sheets

OTHER PUBLICATIONS

European Search Report dated Feb. 4, 2011.
Database WPI Week 200218, Thomson Scientific, London, GB, AN 2002-131271, XP002619038.
Li, Hong-Xia, et al. "Study on ingredients of essential oils of *Curcuma wenyujin* extracted by supercritical-CO2 fluid extraction and steam distillation", Zhong Guo Zhongyao Zazhi—China Journal of Chinese Materia Medica, Zhogguo Yaoxuehui, Beijing, CN, Bd. 31, Nr. 17, Sep. 9, 2006, Seiten 1445-1446, XP009143760, ISSN: 1001-5302.
Jayaprakasha, Guddadarangavvanahally K. et al., "Evaluation of antioxidant activities and antimutagenicity of turmeric oil: A byproduct from curcumin production", Zeitschrift Fuer Naturforschung. C, A Journal of Biosciences, Tuebingen, DE, Bd. 57, Nr. 9-10, Oct. 10, 2002, Seiten 828-835, XP009125905, ISSN: 0939-5075.
Martins, Maria Celia, et al. "Temperature and light effects on turmeric (*Curcuma longa* L.) oleoresin extracts and curcumin", Arquivos de Biologia e Tecnologia, Instituto de Tecnologiado Parana, Curitiba, Br, Bd. 37, Nr. 4, Jan. 1, 1994, Seiten 723-735, XP0091437B8, ISSN: 0365-0979.
Carolina et al. Extraction of Essential Oil and Pigments From *Curcuma longa* [L.] by Steam Distillation and Extraction With Volatile Solvents. Journal of Agric. Food Chem. 2003, 51,6802-6807.

* cited by examiner

BIOACTIVE COMPOSITION FOR COSMETIC APPLICATIONS

CROSS REFERENCE TO RELATED APPLICATION

This application is a divisional of U.S. patent application Ser. No. 12/249,250, filed Oct. 10, 2008 the entire content and disclosure of which is incorporated herein by reference.

FIELD OF THE INVENTION

The invention relates to a process for the preparation of a plant extract from *Curcuma* plants. More particularly, the present invention provides a process for the preparation of a plant extract from Cucuma which includes the following processing steps: A) liquid extraction of *Curcuma* rhizomes, B) optionally, separation of a curcuminoid-containing solid obtained by precipitation from the extraction mixture obtained in process step A), C) removal of solvents present from the extraction mixture obtained in process step A) or B) to obtain a concentrate, and D) distillation of the concentrate at a pressure of less than 1 bar to give the extract as distillate.

BACKGROUND OF THE INVENTION

*Curcuma longa* (*curcuma*, turmeric) is a plant of the ginger plant family (Zigimberaceae), the roots and rhizome of which are used as dye and spice on account of the intense yellow color and the characteristic taste. A variety of biological effects are described for the dried rhizome and extracts therefrom, including stimulation of gastric juice production, anticancer, antioxidative and anti-inflammatory effect. *Curcuma longa* is traditionally used in Ayurvedic medicine, inter alia in topical applications for skin disorders.

The biological effect of *Curcuma longa* and extracts therefrom is generally attributed to the presence of curcuminoids, in particular curcumin, demethoxycurcumin and bisdemethoxycurcumin (cf. Jayaprakasha et al., J. Agric. Food Chem. 2002, 50(13), 3668-3672; Sharma, Biochemical Pharmacology 1976, 25(15), 1811-1812 and U.S. Pat. No. 5,861,415), to which are attributed, besides the antioxidative effect, e.g., anti-inflammatory, antibacterial (Negi et al., J. Agric. Food Chem. 1999, 47(10), 4297-4300), antifungal (Apisariyakul et al., Journal of Ethnopharmacology 1995, 49(3), 163-169), antiparasitic, antimutagenic, anticancer (cf. e.g., Ruby et al., Cancer Letters 1995, 94(1), 79-83; Soudamini et al., Indian Journal of Pharmacology 1988, 20 (2-4), 95-101) and detoxifying properties.

One characteristic property of *Curcuma longa* extracts is the intense yellow color which is caused inter alia by the curcuminoids. Curcuminoids are derived from the curcumin structure

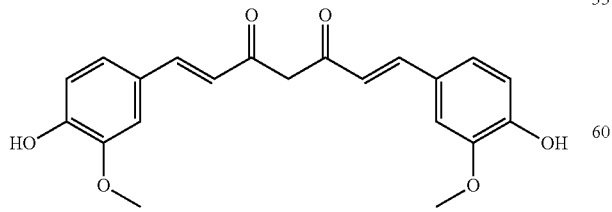

where the substitution pattern on the aromatic rings can vary. Beside curcumin, the best known representatives are demethoxycurcumin

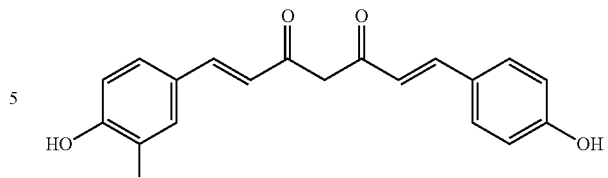

and bisdemethoxycurcumin

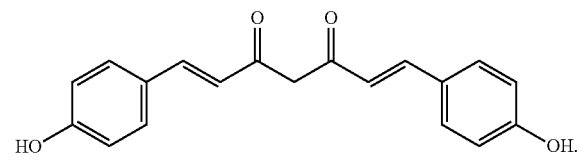 [SMILES: O=C(/C=C/c1ccc(O)cc1)CC(=O)/C=C/c1ccc(O)cc1]

On account of the very intense coloring ability, curcumin is also used as food dye (E100).

On account of the described bioactive effects, curcuminoid-containing extracts, obtained from e.g., *Curcuma longa*, are interesting candidates for active ingredients for topical applications, in particular in cosmetic formulations. However, the intense yellow/orange color stands in the way of one such use; even in concentrations of 0.1% by mass, it causes a significant, unacceptable coloring of creams or lotions.

Kim et al. describe the reduction in the color intensity of *Curcuma aromatica* and *Curcuma longa* extracts through irradiation with gamma radiation (Radiation Physics and Chemistry 2006, 75(3), 449-452). The described process is not suitable for the preparation of cosmetic raw materials since treatment with ionizing radiation is generally not accepted by the market.

SUMMARY OF THE INVENTION

The present invention provides an extract from *Curcuma* which has a significantly reduced color, but still has the described positive biological effects. Moreover, the present invention provides a preparation process that takes place with commercially available processes which are generally accepted for the preparation of cosmetic raw materials.

In general terms, the present invention provides a process for the preparation of a plant extract from *Curcuma* plants which includes:
  A) liquid extraction of *Curcuma* rhizomes,
  B) optionally, separation of a curcuminoid-containing solid obtained by precipitation from the extraction mixture obtained in process step A),
  C) removal of solvents present from the extraction mixture obtained in process step A) or B) to obtain a concentrate, and
  D) distillation of the concentrate at a pressure of less than 1 bar to give the extract as distillate.

DESCRIPTION OF THE INVENTION

Figure 1:
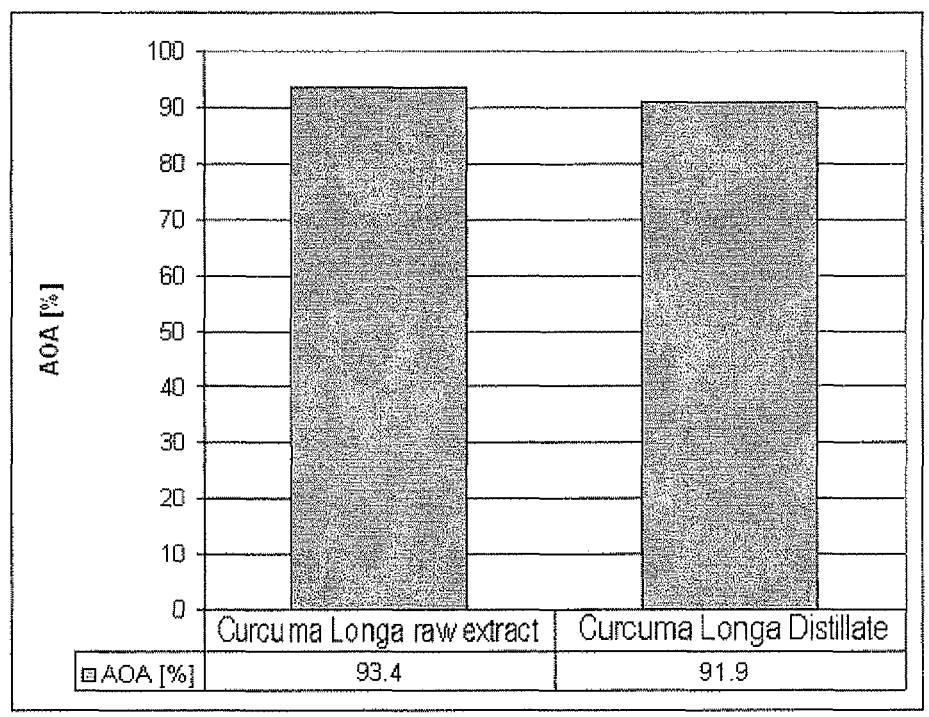
FIG. 1 is a graph illustrating the antioxidative activity of a crude extract and of a distilled extracted from *Curcuma longa* prepared in accordance with the present invention.

Surprisingly, it has now been found that *Curcuma longa* extracts produced by a process according to the present invention have a significantly reduced color.

Thus, the correspondingly prepared extracts can be incorporated into cosmetic formulations without problems in concentrations up to 2% by mass and higher without bringing about a discernible coloration.

Moreover, the extract according to the invention still has the desired bioactive effect, in particular it still has a strong antioxidative effect.

Furthermore, it has been found that the distilled extract of the invention is able to increase the moisture content of the skin, to reduce the number and depth of wrinkles in the skin and to impart a more even, more radiant appearance to the skin.

On account of the attribution, described in the literature, of the biological effects to the (intensely colored) curcuminoids, these properties were not foreseeable.

The extract according to the invention and a process for its preparation are described herein below. Where percentages are stated, these are % by mass, unless stated otherwise.

The invention provides a process for the preparation of a plant extract from *Curcuma* plants, characterized by the following steps: process step A) liquid extraction of *Curcuma* rhizomes, process step B) optionally, separation of a curcuminoid-containing solid obtained by precipitation from the extraction mixture obtained in process step A), process step C) removal of solvents present from the extraction mixture obtained in process step A) or B) to obtain a concentrate and process step D) distillation of the concentrate at a pressure of less than 1 bar to give the extract as a distillate.

The plant raw material used for the preparation of the extract can be the rhizome of *Curcuma* plants, preferably of *Curcuma longa*, which can be pretreated before process step A), by, for example, washing, drying, comminution or grinding. Preferably, the rhizome is in the form of a dry powder after this pretreatment.

For process step A), the generally known processes for solid-liquid extraction can be used, as are described, for example, in *Ullmann's Encyclopedia of Industrial Chemistry*, 7th edition, release 2006 in the chapter "Liquid-Solid Extraction" and in particular in the subchapter "Extraction without chemical reaction". Process step A) can take place batchwise or continuously, in cocurrent, countercurrent or crosscurrent.

Suitable extractants for process step A) are nonpolar to moderately polar solvents, such as, for example, linear or branched cyclic or acyclic alkanes or alkenes (e.g., propane, butane, pentane, hexane, heptane, cyclohexane, petroleum ether), which can optionally be substituted with halogens, in particular chlorine, cyclic or acyclic linear or branched ethers (e.g., diethyl ether, tert-butyl methyl ether, tert-butyl ethyl ether, tetrahydrofuran), primary, secondary or tertiary alcohols, in particular alkanols (e.g., ethanol, isopropanol, n-butanol, tert-butanol, cyclohexanol); esters of short-chain carboxylic acids with short-chain alcohols (e.g., ethyl acetate, butyl acetate, ethyl acetate), ketones (e.g., acetone, methyl isobutyl ketone), or mixtures of at least two of these solvents.

Particularly suitable solvents in process step A) are compressed gases, such as, for example, propane or carbon dioxide, which can be used in the subcritical, near-critical or supercritical phase range. Preferably, in process step A), a supercritical liquid extraction is carried out using compressed gas, particularly preferably compressed $CO_2$. This permits a particularly gentle removal of the extractants. To adjust the properties of these compressed gases, cosolvents such as, for example, ethanol, can optionally be added. Preference is given to using solvents which have no or only slight toxic or other physiologically disadvantageous effects.

Process step A) is preferably carried out at elevated temperature, preferably at a temperature greater than 20° C. and preferably at a temperature of from 30° C. to 80° C.

An optional precipitation step, process step B), can be carried out downstream of process step A); through this, a curcuminoid-rich solid fraction can be separated off from the product obtained in A). The precipitation can be achieved here through partial evaporation of the solvent (concentration) or temperature reduction or combinations thereof. The addition of an antisolvent in which the curcuminoids have only low solubility can likewise be used for the precipitation. For this purpose, preference is given to using substances which have a higher polarity than the solvent used for the extraction step. The solid can be separated off from the remaining solution by customary filtration methods, as are described, for example, in *Ullmann's Encyclopedia of Industrial Chemistry*, 7th edition, release 2006 in the chapter "Filtration".

In process step B), the solid can be separated off as metal complex. For this purpose, a solution of a metal salt, such as, for example, calcium, magnesium, zinc or chromium salt, can be added to the extract from process step A) under elevated temperatures and mixed. The pH can be adjusted to an advantageous value in order to precipitate the metal complex exhaustively. The temperature can be reduced to provide assistance.

In order to simplify the removal of the solvent in process step C) to isolate the crude extract, both in process step A) and also in process step B), the extractants/solvents used have a low boiling point, preferably a boiling point of less than 100° C. under standard conditions.

The removal of extractant/solvent present in process step C) preferably takes place by evaporation. Thus process step C) can take place at ambient pressure, superatmospheric pressure or subatmospheric pressure, where pressure and temperature conditions are to be adapted to the properties of the selected solvent or solvent mixture. If, for the extraction process step A) and the optional precipitation process step B), solvents are used which have boiling temperatures of above about 60° C. at atmospheric pressure, then the vaporization is preferably carried out at reduced pressure, with pressures of from about 100 to <1000 mbar being particularly preferred.

Process step C) can take place either batchwise or continuously.

The removal of the solvent can take place particularly gently in the case of the use of compressed gases as extractants since these already convert to the gaseous state by releasing the superatmospheric pressure and can therefore be evaporated even without applying a sub-atmospheric pressure even at low temperature, e.g., ambient temperature.

Preferably, removal of the solvent in process step C) takes place to a residual content of <1000 ppm of solvent, with residual contents of <100 ppm being particularly preferred.

Plant extracts are mostly complex natural substance mixtures, the biological properties of which are often defined by synergisms, i.e., the effect of the overall extract is greater than the sum of the effect of the individual substances in corresponding concentration. Although the removal of color-imparting components from the extract is an essential constituent of the present invention, a concentration of individual substances, as would be achieved, for example, by fractional distillation, is not necessarily advantageous. For the distillation, preference is therefore given to processes which are characterized by a low number of separation stages.

Moreover, those processes in which the duration of the thermal stress during the distillation is as short as possible are particularly gentle and therefore particularly suitable.

Such distillation methods which have a low number of separation stages and short contact times with hot surfaces are realized, for example, in thin-film evaporators, short-path evaporators, falling-film evaporators or in the case of molecular distillation.

Process step D), distillation at a pressure of less than 1 bar, therefore preferably takes place as molecular distillation, particularly preferably as falling-film distillation, short-path evaporation or thin-film distillation, preferably at a pressure of <10 mbar, in order to largely avoid high thermal stressing of the material. Preferably, process step D) is carried out at a pressure of from $10^{-4}$ to 10 mbar and particularly preferably from about $10^{-3}$ to $10^{-1}$ mbar. Preferably, process step D) is carried out at temperatures of <150° C., particular preference being given here to temperatures of from 70 to 130° C. and in particular of about 100° C.

Very particularly preferably, process step D) is carried out at a temperature of from 97° C. to 103° C. and at a pressure of $10^{-2}$ mbar.

Preferably, process step D) is carried out under conditions under which no new substances are formed, detectable by GC analysis.

In process step D), the ratio of distillate (extract according to the invention) to distillation residue (i.e., the distillation yield) can be controlled through the choice of distillation parameters. High ratios here mean high yields, which offer corresponding economic advantages, on the other hand as the distillate:residue ratio increases, so too does the fraction of color-imparting components in the distillate. A distillate:residue ratio that has proven suitable is from 50:50 to 98:2 parts by weight, with ratios of from 70:30 to 90:10 being preferred and ratios of from 80:20 to 90:10 being particularly preferred.

The extract prepared by the process according to the invention is likewise a constituent of the present invention.

The extract according to the invention preferably has a Gardner color number of <6, preferably <5, particularly preferably <4.

By reference to the examples, it is shown that the extract according to the invention proves itself through several positive properties upon topical application to the skin. Thus, it can increase the moisture content of the skin and also smooth and reduce skin wrinkles. A variety of texture parameters of the skin are advantageously influenced through the use of the extract according to the invention, thus resulting in a more even skin color and a generally improved radiance of the skin.

Consequently, a use of the extract according to the invention for increasing the moisture content of the skin, for reducing and smoothing skin wrinkles, for even skin color or for producing an even appearance of the skin surface is likewise provided by the invention.

Since the extract according to the invention, being an antioxidant, has considerable activity, it can be used as an antioxidative active ingredient. Preferably, the extract according to the invention is used as antioxidative ingredient, in particular as an antioxidative ingredient for reducing skin damage caused by environmental toxins or induced by UV.

On account of its pale color and bioactive properties, the extract according to the invention is exceptionally suitable for the use for the preparation of a cosmetic, dermatological or pharmaceutical formulation. In this regard, there are no fundamental restrictions with regard to the type of formulation used.

The invention thus likewise provides cosmetic, dermatological or pharmaceutical formulations comprising the extract according to the invention.

On account of its solubility in oil, the extract according to the invention can be used in oil phases of oil-based formulations or emulsions, although, in combination with suitable solubilizers, the use in the aqueous phase of water-based formulations or emulsions is also possible. Thus, the extract according to the invention can be used, for example, in lotions and creams (e.g., O/W or W/O emulsions), gel formulations, deodorants (e.g., sticks, emulsions, pump sprays, aerosol sprays, roll-on formulations), oil baths, foam baths, shower gels, shampoos, hair conditioners, liquid soaps, wet wipes, lipsticks, foundations, mouth rinses or toothpastes. So-called leave-on applications are particularly suitable, where it is envisaged that the formulation remains on the skin (e.g., lotions, creams, deodorants). The extract according to the invention can be used here either as the sole active ingredient or in combination with further active ingredients.

The concentration of the extract according to the invention in the cosmetic, dermatological or pharmaceutical formulation is not subject to any principle technical limits, although at concentrations above about 5% (depending on the type of formulation), a characteristic odor of the extract is clearly perceptible. Consequently, the extract according to the invention is used in the formulations preferably in concentrations of from 0.01 to 5%, particularly preferably in concentrations of from 0.05 to 1%.

The cosmetic, dermatological or pharmaceutical formulations and also the care and cleansing compositions can comprise, for example, at least one additional component selected from the group of:

emollients,
emulsifiers and surfactants,
thickeners/viscosity regulators/stabilizers,
UV photoprotective filters,
antioxidants and vitamins,
hydrotropes (or polyols),
solids and fillers,
film formers,
pearlescence additives,
deodorant and antiperspirant active ingredients,
insect repellents,
self-tanning agents,
preservatives,
conditioners,
perfumes,
dyes,
biogenic active ingredients,
care additives,
super fatting agents,
solvents.

Emollients that can be used are all cosmetic oils, in particular mono- or diesters of linear and/or branched mono- and/or dicarboxylic acids having 2 to 44 carbon atoms with linear and/or branched saturated or unsaturated alcohols having 1 to 22 carbon atoms. It is likewise possible to use the esterification products of aliphatic, difunctional alcohols having 2 to 36 carbon atoms with monofunctional aliphatic carboxylic acids having 1 to 22 carbon atoms. Furthermore, long-chain acrylic acid esters, such as, for example, esters of benzoic acid, e.g., benzoic acid esters of linear or branched, saturated or unsaturated alcohols having 1 to 22 carbon atoms, or else isostearyl benzoate or octyldodecyl benzoate. Further monoesters suitable as emollients and oil components are, for example, the methyl esters and isopropyl esters of fatty acids having 12 to 22 carbon atoms, such as, for example, methyl laurate, methyl stearate, methyl oleate, methyl erucate, isopropyl palmitate, isopropyl myristate, isopropyl stearate, isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and esters which are obtainable from technical-grade aliphatic alcohol cuts and technical-grade, aliphatic carboxylic acid mixtures, e.g., esters of unsaturated fatty alcohols having 12 to 22 carbon atoms and saturated or unsaturated fatty acids having 12 to 22 carbon atoms, as are accessible from animal and vegetable fats. Also suitable, however, are naturally occurring monoester and/or wax ester mixtures, as are present, for example, in jojoba oil or in sperm oil. Suitable dicarboxylic acid esters are, for example, di-n-butyl adipate, di-n-butyl sebacate, di (2-ethylhexyl) adipate, di (2-hexyldecyl) succinate, diisotridecyl azelate. Suitable diol esters are, for example, ethylene glycol dioleate, ethylene glycol diisotridecanoate, propylene glycol di(2-ethylhexanoate), butanediol diisostearate, butanediol dicaprylate/caprate and neopentyl-glycol dicaprylate. Further, fatty acid esters which can be used as emollients are, for example, $C_{12-15}$ alkyl benzoate, dicaprylyl carbonate, diethylhexyl carbonate. As emollients and oil component it is likewise possible to use relatively long-chain triglycerides, i.e., triple esters of glycerol with three acid molecules, of which at least one is relatively long-chain. Mention may be made here by way of example of fatty acid triglycerides; as such, natural, vegetable oils, e.g., olive oil, sunflower oil, soy oil, peanut oil, rapeseed oil, almond oil, sesame oil, avocado oil, castor oil, coco butter, palm oil, but also the liquid fractions of coconut oil or of palm kernel oil, and also animal oils such as, for example, shark liver oil, cod liver oil, whale oil, beef tallow and butter fat, waxes, such as beeswax, carnauba palm wax, spermaceti, lanolin and neatsfoot oil, the liquid fractions of beef tallow or else synthetic triglycerides of caprylic/capric acid mixtures, triglycerides of technical-grade oleic acid, triglycerides with isostearic acid, or of palmitic acid/oleic acid mixtures, for example, can be used as emollients and oil components. Furthermore, hydrocarbons, in particular including liquid paraffins and isoparaffins, can be used. Examples of hydrocarbons that can be used are paraffin oil, isohexadecane, polydecene, Vaseline, paraffinum perliquidum, squalane, ceresin. Furthermore, it is possible to use linear or branched fatty alcohols, such as oleyl alcohol or octyldodecanol, and also fatty alcohol ethers, such as dicaprylyl ether. Suitable silicone oils and silicone waxes are, for example, polydimethylsiloxanes, cyclomethylsiloxanes, and also aryl- or alkyl- or alkoxy-substituted polymethylsiloxanes or cyclomethylsiloxanes. Further suitable oil bodies are, for example, Guerbet alcohols based on fatty alcohols having 6 to 18, preferably 8 to 10, carbon atoms, esters of linear $C_6$-$C_{22}$-fatty acids with linear $C_6$-$C_{22}$-fatty alcohols, esters of branched $C_6$-$C_{13}$-carboxylic acids with linear $C_6$-$C_{22}$-fatty alcohols, esters of linear $C_6$-$C_{22}$-fatty acids with branched $C_8$-$C_{18}$-alcohols, in particular 2-ethylhexanol or isononanol, esters of branched $C_6$-$C_{13}$-carboxylic acids with branched alcohols, in particular 2-ethylhexanol or isononanol, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, vegetable oils, branched primary alcohols, substituted cyclohexanes, linear $C_6$-$C_{22}$-fatty alcohol carbonates, Guerbet carbonates, esters of benzoic acid with linear and/or branched $C_6$-$C_{22}$-alcohols (e.g., Finsolv™ TN), dialkyl ethers, ring-opening products of epoxidized fatty acid esters with polyols, silicone oils and/or aliphatic and/or naphthenic hydrocarbons.

Emulsifiers or surfactants that can be used are nonionic, anionic, cationic or amphoteric surfactants.

Nonionogenic emulsifiers or surfactants that can be used are compounds from at least one of the following groups:
  addition products of from 2 to 100 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
  $C_{12/18}$-fatty acid mono- and diesters of addition products of from 1 to 100 mol of ethylene oxide onto glycerol,
  glycerol mono- and -diesters and sorbitan mono- and diesters of saturated and unsaturated fatty acids having 6 to 22 carbon atoms and ethylene oxide addition products thereof,
  alkyl mono- and oligoglycosides having 8 to 22 carbon atoms in the alkyl radical and ethylene oxide addition products thereof,
  addition products of from 2 to 200 mol of ethylene oxide onto castor oil and/or hydrogenated castor oil,
  partial esters based on linear, branched, unsaturated or saturated $C_6$-$C_{22}$-fatty acids, ricinolic acid, and 12-hydroxystearic acid and glycerol, polyglycerol, pentaerythritol, dipentaerythritol, sugar alcohols (e.g., sorbitol) alkyl glycosides (e.g., methyl glucoside, butyl glucoside, lauryl glucoside) and polyglucosides (e.g., cellulose),
  mono-, di- and trialkyl phosphates, and mono-, di- and/or tri-PEG-alkyl phosphates and salts thereof,
  polysiloxane-polyether copolymers (dimethicone copolyols), such as, for example, PEG/PPG-20/6 dimethicone, PEG/PPG-20/20 dimethicone, bis-PEG/PPG-20/20 dimethicone, PEG-12 or PEG-14 dimethicone, PEG/PPG-14/4 or 4/12 or 20/20 or 18/18 or 17/18 or 15/15,
  polysiloxane-polyalkyl-polyether copolymers or corresponding derivatives, such as, for example, lauryl or cetyl dimethicone copolyols, in particular cetyl PEG/PPG-10/1 dimethicone (ABIL® EM 90 (Degussa)),
  mixed esters of pentaerythritol, fatty acids, citric acid and fatty alcohol as in DE 11 65 574 and/or mixed esters of fatty acids having 6 to 22 carbon atoms, methyl glucose and polyols, such as, for example, glycerol or polyglycerol,
  citric acid esters, such as, for example, glyceryl stearate citrate, glyceryl oleate citrate and dilauryl citrate.

Anionic emulsifiers or surfactants can comprise water-solubilizing anionic groups, such as, for example, a carboxylate, sulphate, sulphonate or phosphate group, and a lipophilic radical. Skin-compatible anionic surfactants are known to the person skilled in the art in a large number and are commercially available. These may be alkyl sulphates or alkyl phosphates in the form of their alkali metal, ammonium or alkanolammonium salts, alkyl ether sulphates, alkyl ether carboxylates, acyl sarcosinates, and also sulphosuccinates and acyl glutamates in the form of their alkali metal or ammonium salts.

Cationic emulsifiers and surfactants can also be added. As such, in particular quaternary ammonium compounds, in particular those provided with at least one linear and/or branched, saturated or unsaturated alkyl chain having 8 to 22 carbon atoms, can be used, such as, for example, alkyltrimethylammonium halides, such as, for example, cetyl-trimethylammonium chloride or bromide or behenyltrimethylammonium chloride, but also dialkyldimethylammonium halides, such as, for example, distearyldimethylammonium chloride, can be used.

Furthermore, monoalkylamidoquats, such as, for example, palmitamido-propyltrimethylammonium chloride, or corresponding dialkylamidoquats can be used.

Furthermore, it is also possible to use readily biodegradable quaternary ester compounds, which may be quaternized fatty acid esters based on mono-, di- or triethanolamine. Furthermore, alkylguanidinium salts can be added as cationic emulsifiers.

Typical examples of mild, i.e., particularly skin-compatible surfactants are fatty alcohol polyglycol ether sulphates, monoglyceride sulphates, mono- and/or dialkyl-sulphosuccinates, fatty acid isethionate, fatty acid sarcosinates, fatty acid taurides, fatty acid glutamates, ether carboxylic acids, alkyl oligoglucosides, fatty acid glucamides, alkylamidobetaines and/or protein fatty acid condensates, the latter for example based on wheat proteins.

Furthermore, it is possible to use amphoteric surfactants, such as, for example, betaines, amphoacetates or amphopropionates, thus, for example, substances such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having 8 to 18 carbon atoms in alkyl or acyl group, and also cocoacylaminoethyl hydroxyethylcarboxymethylglycinate.

Of the ampholytic surfactants, it is possible to use those surface-active compounds which, apart from a $C_8/C_{18}$-alkyl or -acyl group in the molecule, contain at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 18 carbon atoms in the alkyl group. Further examples of ampholytic surfactants are N-cocoalkylaminopropionate, cocoacylaminoethylaminopropionate and $C_{12}/_{18}$-acylsarcosine.

Suitable thickeners are, for example, polysaccharides, in particular xanthan gum, guar guar, agar agar, alginates and tyloses, carboxymethylcellulose and hydroxyethylcellulose, also relatively high molecular weight polyethylene glycol mono- and diesters of fatty acids, polyacrylates, (e.g., Carbopole™ or Synthalene™), polyacrylamides, polyvinyl alcohol and polyvinylpyrrolidone, surfactants, such as, for example, ethoxylated fatty acid glycerides, esters of fatty acids with polyols, such as, for example, pentaerythritol or trimethylolpropane, fatty alcohol ethoxylates with a narrowed homologue distribution or alkyl oligoglucosides, and also electrolytes such as sodium chloride and ammonium chloride.

Suitable thickeners for thickening oil phases are all thickeners known to the person skilled in the art. In particular, mention is to be made here of waxes, such as hydrogenated castor wax, beeswax or microwax. Furthermore, it is also possible to use inorganic thickeners, such as silica, alumina or sheet silicates (e.g., hectorite, laponite, saponite). These inorganic oil phase thickeners may be hydrophobically modified. For the thickening/stabilization of water-in-oil emulsions, use can be made here in particular of aerosils, sheet silicates and/or metal salts of fatty acids, such as, for example zinc stearate.

As viscosity regulators for aqueous surfactant systems, e.g., NaCl, low molecular weight nonionic surfactants, such as cocoamides DEA/MEA and laureth-3, or polymeric, high molecular weight, associative, highly ethoxylated fatty derivatives, such as PEG-200 hydrogenated glyceryl palmate may be present.

UV photoprotective filters that can be used are, for example, organic substances which are able to absorb ultraviolet rays and give off the absorbed energy again in the form of longer-wave radiation, e.g., heat. UVB filters may be oil-soluble or water-soluble. Oil-soluble UVB photoprotective filters to be mentioned are, for example:

3-benzylidenecamphor and derivatives thereof, e.g., 3-(4-methyl-benzylidene)camphor, 4-aminobenzoic acid derivatives, such as, for example 2-ethylhexyl 4-(dimethylamino)benzoate, 2-ethylhexyl 4-(dimethylamino)benzoate and amyl 4-(dimethyl-amino)benzoate, esters of cinnamic acid, such as, for example 2-ethylhexyl 4-methoxycinnamate, isopentyl 4-methoxycinnamate, 2-ethylhexyl 2-cyano-3-phenylcinnamate (octocrylene), esters of salicylic acid, such as, for example, 2-ethylhexyl salicylate, 4-isopropylbenzyl salicylate, homomethyl salicylate, derivatives of benzophenone, such as, for example, 2-hydroxy-4-methoxybenzophenone, 2-hydroxy-4-methoxy-4'-methylbenzophenone, 2,2'-dihydroxy-4-methoxybenzophenone, esters of benzalmalonic acid, such as, for example, di-2-ethylhexyl 4-methoxybenzmalonate, triazine derivatives, such as, for example, 2,4,6-trianilino (p-carbo-2'-ethyl-1'-hexyloxy)-1,3,5-triazine and octyltriazone, propane-1,3-diones, such as, for example, 1-(4-tert-butylphenyl)-3-(4'-methoxyphenyl)propane-1,3-dione.

Suitable water-soluble UVB photoprotective filters are:

2-phenylbenzimidazole-5-sulphonic acid and the alkali metal, alkaline earth metal, ammonium, alkylammonium, alkanolammonium and glucammonium salts thereof, sulphonic acid derivatives of benzophenone, such as, for example, 2-hydroxy-4-methoxybenzophenone-5-sulphonic acid and its salts, sulphonic acid derivatives of 3-benzylidenecamphor, such as, for example 4-(2-oxo-3-bornylidenemethyl)benzenesulphonic acid and 2-methyl-5-(2-oxo-3-bornylidene)sulphonic acid and salts thereof.

Suitable typical UVA photoprotective filters are, in particular, derivatives of benzoylmethane, such as, for example, 1-(4'-tert-butylphenyl)-3-(4'-methoxyphenyl)-propane-1,3-dione or 1-phenyl-3-(4'-isopropylphenyl)propane-1,3-dione. The UV-A and UV-B filters can of course also be used in mixtures.

Besides the specified soluble substances, insoluble pigments are also suitable for this purpose, namely finely dispersed metal oxides and/or salts, such as, for example, titanium dioxide, zinc oxide, iron oxide, aluminium oxide, cerium oxide, zirconium oxide, silicates (talc), barium sulphate and zinc stearate. Here, the particles should have an average diameter of less than 100 nm, e.g., between 5 and 50 nm and in particular between 15 and 30 nm They can have a spherical shape, although it is also possible to use those particles which have an ellipsoidal size or a shape which deviates in some other way from the spherical configuration. A relatively new class of photoprotective filters is micronized organic pigments, such as, for example, 2,2'-methylenebis{6-(2H-benzotriazol-2-yl)-4-(1,1,3,3-tetra-methylbutyl)phenol} with a particle size of <200 nm, which is available, for example, as 50% strength aqueous dispersion.

Further suitable UV photoprotective filters can be found in the overview by P. Finkel in SÖFW-Journal 122, 543 (1996).

Besides the two aforementioned groups of primary UV photoprotective filters, it is also possible to use secondary photoprotective agents of the antioxidant type, which interrupt the photochemical reaction chain which is triggered when UV radiation penetrates into the skin.

Antioxidants and vitamins that can be used are, for example, superoxide dismutase, tocopherol (vitamin E), tocopherol sorbate, tocopherol acetate, other esters of tocopherol, dibutylhydroxytoluene and ascorbic acid (vitamin C) and its salts, and also derivatives thereof (e.g., magnesium ascorbyl phosphate, sodium ascorbyl phosphate, ascorbyl sorbate), ascorbyl esters of fatty acids, butylated hydroxybenzoic acid and its salts, peroxides such as, for example, hydrogen peroxide, perborates, thioglycolates, persulphate salts, 6-hydroxy-2,5,7,8-tetramethylchroman-2-carboxylic acid (TROLOX®), gallic acid and its alkyl esters, uric acid and its salts and alkyl esters, sorbic acid and its salts, lipoic acid, ferulic acid, amines (e.g., N,N-diethylhydroxylamine, amino-guanidine), sulphhydryl compounds (e.g., glutathione), dihydroxyfumaric acid and its salts, glycine pidolate, arginine pilolate, nordihydroguaiaretic acid, bioflavonoids, curcumin, lysine, L-methionine, proline, superoxide dismutase, silymarin, tea extract, grapefruit peel/pip extract, melanin, rosemary extract, thioctanoic acid, resveratrol, oxyresveratrol, etc.

Hydrotropes that can be used for improving the flow behaviour and the application properties are, for example, ethanol, isopropyl alcohol or polyols. Polyols that are suitable here can have 2 to 15 carbon atoms and at least two hydroxyl groups. Typical examples are:

glycerol, alkylene glycols, such as, for example, ethylene glycol, diethylene glycol, propylene glycol, butylene glycol, hexylene glycol, and also polyethylene glycols with an average molecular weight of from 100 to 1000 daltons, technical-grade oligoglycerol mixtures with a degree of autocondensation of from 1.5 to 10, such as, for example, technical-grade diglycerol mixtures with a diglycerol content of from 40 to 50% by weight, methylol compounds, such as, in particular, trimethylolethane, trimethylolpropane, trimethylolbutane, pentaerythritol and dipentaerythritol, lower alkyl glucosides, in particular those with 1 to 4 carbon atoms in the alkyl radical, such as, for example, methyl and butyl glucoside, sugar alcohols having 5 to 12 carbon atoms, such as, for example, sorbitol or mannitol, sugars having 5 to 12 carbon atoms, such as, for example, glucose or sucrose, amino sugars, such as, for example, glucamine Solids that can be used are, for example, iron oxide pigments, titanium dioxide or zinc oxide particles and those specified additionally under "UV protectants". Furthermore, it is also possible to use particles which lead to special sensory effects, such as, for example, nylon-12, boron nitride, polymer particles, such as, for example, polyacrylate or polymethylacrylate particles or silicone elastomers. Fillers that can be used include starch and starch derivatives such as tapioca starch, distarch phosphate, aluminium and sodium starch, octenyl succinate, and pigments which have neither primarily a UV filter nor coloring effect, for example Aerosils® (CAS No. 7631-86-9).

Film-formers for, for example, improving the water resistance that can be used are, for example: polyurethane, dimethicones, copolyol, polyacrylates or PVP/VA copolymer (PVP=polyvinylpyrrolidone, VA=vinyl acetate). Fat-soluble film formers that can be used are: e.g. polymers based on polyvinylpyrrolidone (PVP), copolymers of polyvinylpyrrolidone, PVP/hexadecane copolymer or PVP/eicosene copolymer.

Pearlescence additives that can be used are, for example, glycol distearates or PEG-3 distearate.

Suitable deodorant active ingredients are, for example, odor concealers such as the customary perfume constituents, odor absorbers, for example the sheet silicates described in the patent laid-open specification DE 40 09 347, of these in particular montmorillonite, kaolinite, illite, beidelite, nontronite, saponite, hectorite, bentonite, smectite, also, for example, zinc salts of ricinolic acid.

Antimicrobial agents are likewise suitable for being incorporated. Antimicrobial substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbonilide, quaternary ammonium compounds, clove oil, mint oil, thyme oil, trethyl citrate, farnesol (3,7,11-trimethyl-2,6,10-dodecatrien-1-ol), ethylhexyl glyceryl ether, polyglyceryl-3 caprylate (TEGO® Cosmo P813, Evonik), and also the active agents described in the patent laid-open specifications DE 198 55 934, DE 37 40 186, DE 39 38 140, DE 42 04 321, DE 42 29 707, DE 42 29 737, DE 42 38 081, DE 43 09 372, DE 43 24 219 and EP 666 732.

Antiperspirant active ingredients that can be used are astringents, for example basic aluminium chlorides, such as aluminium chlorohydrate ("ACH") and aluminium zirconium glycine salts ("ZAG").

Insect repellents that can be used are, for example, N,N-diethyl-m-toluamide, 1,2-pentanediol or Insect Repellent 3535.

Self-tanning agents that can be used are, for example, dihydroxyacetone and erythrulose.

Preservatives that can be used are, for example, mixtures of single or multiple alkyl paraben esters with phenoxyethanol. The alkyl paraben esters may be methyl paraben, ethyl paraben, propyl paraben and/or butyl paraben. Instead of phenoxyethanol, it is also possible to use other alcohols, such as, for example, benzyl alcohol or ethanol. Moreover, other customary preservative, such as, for example, sorbic acid or benzoic acid, salicylic acid, 2-bromo-2-nitropropane-1,3-diol, chloroacetamide, diazolidinylurea, DMDM hydantoin, iodopropynyl butyl-carbamate, sodium hydroxymethylglycinate, methyl-isothiazoline, chloromethyl isothiazoline, ethylhexylglycerol or caprylyl glycol, can also be used. Conditioners that can be used are, for example, organic quaternary compounds such as cetrimonium chloride, dicetyldimonium chloride, behentrimonium chloride, distearyldimonium chloride, behentrimonium methosulphate, distearoylethyldimonium chloride, palmitamidopropyltrimonium chloride, guar hydroxypropyltrimonium chloride, hydroxypropylguar hydroxypropyltrimonium chloride, or quaternium-80, or else amine derivatives, such as, for example aminopropyldimethicones or stearamidopropyldimethyl-amines.

Perfumes that can be used are natural or synthetic fragrances or mixtures thereof. Natural fragrances are extracts from flowers (lily, lavender, roses, jasmine, neroli, ylang ylang), stems and leaves (geranium, patchouli, petit grain), fruits (anis, coriander, caraway, juniper), fruit peels (bergamot, lemon, orange), roots (mace, angelica, celery, cardamom, costus, iris, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester type, ether type, aldehyde type, ketone type, alcohol type and hydrocarbon type. Fragrance compounds of the ester type are, for example, benzyl acetate, phenoxyethyl isobutyrate, p-tert-butyl cyclohexyl acetate, linalyl acetate, dimethylbenzyl-carbonyl acetate, phenylethyl acetate, linalyl benzoate, benzyl formate, ethylmethylphenyl glycinate, allyl cyclohexylpropionate, styrallylpropionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones, α-isomethylionone and methyl cedryl ketone, the alcohols include acnethole, citronellol, eugenol, isoeugenol, geraniol, linalool, phenylethyl alcohol and terpineol, the hydrocarbons include primarily the terpenes and balsams. It is also possible to use mixtures of different fragrances which together produce a pleasant scent note. Essential oils of relatively low volatility, which in most cases are used as aroma components, are also suitable as perfumes, e.g., sage oil, camomile oil, clove oil, melissa oil, mint oil, cinnamon leaf oil, linden blossom oil, juniper berry oil, vetiver oil, olibanum oil, galbanum oil, labolanum oil and lavandin oil. Bergamot oil, dihydromyrcenol, lilial, lyral, citronellol, phenylethyl alcohol, α-hexylcinnamaldehyde, geraniol, benzyl acetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat, alone or in mixtures, can be used.

Dyes that can be used are the substances approved and suitable for cosmetic purposes, as are listed, for example, in the publication "Kosmetische Färbemittel" [Cosmetic Colorants] from the Dyes Commission of the German Research Society, Verlag Chemie, Weinheim, 1984, pp. 81 to 106. These dyes are usually used in concentrations of from 0.001 to 0.1% by weight, based on the total mixture.

Biogenic active ingredients are to be understood as meaning, for example, tocopherol, tocopherol acetate, tocopherol palmitate, ascorbic acid, polyphenols, deoxyribonucleic acid, coenzyme Q10, retinol, AHA acids, amino acids, hyaluronic acid, alpha-hydroxy acids, isoflavones, polyglutamic acid, creatine (and creatine derivatives), guanidine (and guanidine derivatives), pseudoceramides, essential oils, peptides, protein hydrolysates, plant extracts, bisabolol, allantoin, panthenol, phytantriol, idebenone, liquorice extract, glycyrrhizidine, scleroglucan, β-glucan, santalbic acid and vitamin complexes.

Examples of plant extracts are horse chestnut extract, camomile extract, rosemary extract, black and red currant extract, birch extract, rosehip extract, algae extracts, green tea extract, aloe extract, ginseng extract, gingko extract, grapefruit extract, calendula extract, camphor, thyme extract, mangosteen extract, cystus extract, *Terminalia arjuna* extract, oat extract, oregano extract, raspberry extract, strawberry extract, etc.

The biogenic active ingredients can also include the so-called barrier lipids, for which, by way of example, ceramides, phytosphingosine and derivatives, sphingosine and derivatives, sphinganine and derivatives, pseudoceramides, phospholipids, lysophospholipids, cholesterol and derivatives, cholesteryl esters, free fatty acids, lanolin and derivatives, squalane, squalene and related substances are mentioned.

Within the context of the invention, the biogenic active ingredients also include antiacne, such as, for example, benzoyl peroxide, phytosphingosine and derivatives, niacinamide hydroxybenzoate, nicotinaldehyde, retinoic acid and derivatives, salicylic acid and derivatives, citronellic acid, etc., and anticellulite, such as, for example, xanthine compounds such as caffeine, theophylline, theobromine and aminophylline, carnitine, carnosine, salicyloyl phytosphingosine, phytosphingosines, santalbic acid etc., as are antidandruff agents such as, for example, salicylic acid and derivatives, zinc pyrithione, selenium sulphide, sulphur, ciclopiroxolamine, bifonazole, climbazole, octopirox and actirox etc. as are astringents such as, for example, alcohol, aluminium derivatives, gallic acid, pyridoxine salicylate, zinc salts such as, for example, zinc sulphate, acetate, chloride, lactate, zirconium chlorohydrate etc. Bleaches such as kojic acid, arbutin, vitamin C and derivatives, hydroquinone, turmeric oil, creatinine, sphingolipids, niacinamide, etc. can likewise be included in the biogenic active ingredients.

Care additives that may be present are, for example, ethoxylated glycerol fatty acid esters, such as, for example, PEG-7 glycerol cocoate, or cationic polymers, such as, for example, polyquaternium-7 or polyglycerol esters.

Super fatting agents that can be used are substances such as, for example lanolin and lecithin, and also polyethoxylated or acylated lanolin and lecithin derivatives, polyol fatty acid esters, monoglycerides and fatty acid alkanolamides, where the latter simultaneously serve as foam stabilizers.

Solvents that can be used are, for example, aliphatic alcohols, such as ethanol, propanol or 1,3-propanediol, cyclic carbonates, such as ethylene carbonate, propylene carbonate, glycerol carbonate, esters of mono- or polycarboxylic acids, such as ethyl acetate, ethyl lactate, dimethyl adipate and diethyl adipate, propylene glycol, dipropylene glycol, glycerol, glycerol carbonate or water.

In the examples listed below, the present invention is described by way of example without any intention to limit the invention, the scope of application of which arises from the entire description and the claims, to the embodiments specified in the examples.

Example 1

The preparation of a distilled *Curcuma longa* extract by thin-film distillation is described below.

1 kg of dried, comminuted rhizome of *Curcuma longa* was extracted continuously with $CO_2$ for 4 h at 300 bar and 40° C. to exhaustion. The crude extract was obtained through expansion of the $CO_2$/extract mixture to ambient pressure into a cold-trap. The extraction was repeated several times, with yields of about 45-50 g of extract being obtained per kg of dry rhizome. The extract was an intensely orange-colored oil with a Gardner color number of 11.3 which had a characteristic odor.

200 g of the extract were distilled over a thin-film evaporator with external heating surface at a temperature of 100° C. and a pressure of $10^{-2}$ mbar. 162 g of a yellowish, clear liquid (Gardner color number 3.5) were obtained as distillate, and 33 g of a dark, cloudy oil were obtained as residue. The distilled extract was used for the formulation and effectiveness experiments described below (Examples 3-6).

Example 2

The following example illustrates the connection between distillation yield and color of the distilled extract. The procedure was analogous to that in Example 1, except the temperature of the vaporization surface was varied in the range from 90 to 110° C. The results are shown in the table below:

| Vaporization temperature/° C.: | 90 | 100 | 110 |
|---|---|---|---|
| Distillation yield/% | 69 | 74 | 87 |
| Color number (Gardner): | 3.2 | 3.4 | 3.7 |

Example 3

The influence of the addition of *Curcuma longa* crude extract and of the distilled extract according to the invention to cosmetic formulations on the color is shown below.

Various cosmetic formulations with the crude extract and with the distillate were prepared. Furthermore, the blank formulation without extract was prepared. The color of these formulations was determined. For this, the CIE-Lab color space was used as a basis. By stating the L*a*b* values it is possible to determine a color precisely. The axes in the Lab space correspond directly to perceptible properties of the colors. The red(+a)/green(−a) values are spread along the "a" axis, and the yellow(+b)/blue(−b) values are on the "b" axis (cf. DIN 6174).

F1. O/W lotion with 0.5% *Curcuma longa* extract

|  | F1-A | F1-B | F1-C |
|---|---|---|---|
| Decyl oleate | 5.7% | 5.7% | 5.7% |
| Ethylhexyl stearate | 6.5% | 6.5% | 6.5% |
| Glyceryl stearate | 0.5% | 0.5% | 0.5% |
| Stearic acid | 0.7% | 0.7% | 0.7% |
| Cetearyl glucoside | 1.0% | 1.0% | 1.0% |
| Creatine | 0.5% | 0.5% | 0.5% |
| Glycerol | 3.0% | 3.0% | 3.0% |
| Kathon CG | 0.015% | 0.015% | 0.015% |
| Water | 80.385% | 79.885% | 79.885% |
| Carbomer | 0.2% | 0.2% | 0.2% |
| Ethylhexyl stearate | 0.8% | 0.8% | 0.8% |
| NaOH (10%) | 0.7% | 0.7% | 0.7% |
| *Curcuma longa* crude extract | — | 0.5% | — |
| *Curcuma longa* dest. | — | — | 0.5% |

F2. O/W cream with 0.5% *Curcuma longa* extract

|  | F2-A | F2-B | F2-C |
|---|---|---|---|
| Glyceryl stearate | 2.5% | 2.5% | 2.5% |
| Stearic acid | 1.0% | 1.0% | 1.0% |
| Stearyl alcohol | 1.5% | 1.5% | 1.5% |
| Decyl cocoate | 8.0% | 8.0% | 8.0% |
| Ethylhexyl stearate | 7.0% | 7.0% | 7.0% |
| Caprylic/capric triglyceride | 5.0% | 5.0% | 5.0% |
| Cetearyl glucoside | 1.0% | 1.0% | 1.0% |
| Glycerol | 3.0% | 3.0% | 3.0% |
| Kathon CG | 0.015% | 0.015% | 0.015% |
| Water | 64.235% | 63.735% | 63.735% |
| Carbomer | 0.2% | 0.2% | 0.2% |
| Ethylhexyl stearate | 0.8% | 0.8% | 0.8% |
| NaOH (10%) | 0.75% | 0.75% | 0.75% |
| Polyglutamic acid; hydrolysed sclerotium gum; betaine; urea; potassium lactate | 5.0% | 5.0% | 5.0% |
| *Curcuma longa* crude extract | — | 0.5% | — |
| *Curcuma longa* dest. | — | — | 0.5% |

F3. W/O lotion with 0.5% *Curcuma longa* extract

|  | F3-A | F3-B | F3-C |
|---|---|---|---|
| Cetyl PEG/PPG-10/1 dimethicone | 2.0% | 2.0% | 2.0% |
| Ceresine | 0.5% | 0.5% | 0.5% |
| Hydrogenated castor oil | 0.5% | 0.5% | 0.5% |
| Decyl oleate | 9.0% | 9.0% | 9.0% |
| Caprylic/capric triglyceride | 10.0% | 10.0% | 10.0% |
| Diethylhexyl carbonate | 5.0% | 5.0% | 5.0% |
| PPG-3 myristyl ether; salicyloyl phytosphingosine | 3.0% | 3.0% | 3.0% |
| Water | 69.485% | 68.985% | 68.985% |
| Sodium chloride | 0.5% | 0.5% | 0.5% |
| Kathon CG | 0.015% | 0.015% | 0.015% |
| *Curcuma longa* crude extract | — | 0.5% | — |
| *Curcuma longa* dest. | — | — | 0.5% |

The formulations with the undistilled crude extract (F1-B, F2-B and F3-B) had a clearly perceptible yellow color whereas the formulations prepared with the distilled extract according to the invention (F1-C, F2-C and F3-C) could not be differentiated from the blank formulations (F1-A, F2-A and F3-A). The visual impression was confirmed by color measurements.

The table below gives the values for a* and b* for the various test formulations.

|  |  | Without extract | Crude extract | Distillate |
|---|---|---|---|---|
| Example 1 | a* | −0.7 | −2.5 | −0.8 |
|  | b* | 0.5 | 5.9 | 0.8 |
| Example 2 | a* | −0.8 | −3.2 | −0.9 |
|  | b* | 0.8 | 7.7 | 1.1 |
| Example 3 | a* | −0.3 | −2.7 | −0.5 |
|  | b* | 0.7 | 7 | 1 |

Particularly in the case of the b* value, there was a significant shift into the yellow range when the formulation comprises the crude extract. By contrast, for the formulation with the distillate, a b* value was obtained which was virtually identical to that for the blank formulation.

Example 4

In the case of the a* value as well, a shift into the green range was found with the crude extract. Here too, the blank formulation and the formulation with the distillate exhibit virtually identical values.

The antioxidative effectiveness of the *Curcuma longa* extract was investigated with the help of the so-called β-carotene test. In this test, it is ascertained to what extent an antioxidant inhibits the coupled autooxidation of linoleic acid and β-carotene. This reaction can be monitored photometrically from the carotene degradation.

The substance to be investigated was dissolved to give a 5% strength in methanol. In a further step, 3 mg of β-carotene, 400 mg of linoleic acid and 4.0 g of Tween 40 were mixed with gentle heating until the β-carotene had dissolved. 0.2200 g of this mixture was solubilized in 25 ml of warm water (50° C.). 13 µl of the methanolic solution and 1000 µm of solubilisate were mixed. As control, 13 µm of methanol were mixed with 1000 µl of solubilisate. The absorbance of these solutions was measured at one minute intervals at 470 nm and 50° C. The antioxidative activity (AOA) was calculated as percentage inhibition based on the control for the time interval from 20-40 min. The AOA was calculated according to the following formula:

$$AOA=100*(DRc-DRs)/(DRc)$$

DRc=degradation rate of the control

DRs=degradation rate of the sample

FIG. 1 gives the antioxidative activity of the crude extract and of the distilled extract from *Curcuma longa*.

The result shows that the ability of the extract to inhibit the degradation of β-carotene was not significantly impaired by the distillation and accordingly the distilled extract according to the invention also had an excellent antioxidative effect.

Example 5

The following example illustrates the moisturizing properties of the distilled extract, i.e., the ability to increase the moisture content of the skin.

The skin moisture was determined using a corneometer. In the corneometer principle, the skin moisture of the "external layer" of the epidermis (stratum corneum) was determined by a capacity measurement. This principle is based on the fact that water and other substances have different dielectric constant. An appropriately shaped measuring capacitor reacts to the samples introduced into its measuring volume with varying capacity changes which were collected and evaluated completely automatically by the instrument. The active probe coated with special glass was pressed onto the area of skin to be measured and, after one second, the corneometer measurement, i.e., the degree of moisture on the surface of the skin, appeared on the display (www.dermatest.de/de/ueberuns.html).

In order to investigate the long-term effect of the moisturizing properties of the distillate, a four-week study with 30 subjects was carried out. The skin moisture was determined using a CM 825 corneometer (Courage & Khazaka). Prior to each measurement, the subjects had to remain in a climatically controlled room (21-22° C., 55% relative humidity) for at least 15 min The subjects were divided into two groups. The first group received the test formulation with 0.5% of the distilled extract according to the invention (F4-B), and the second group received the formulation without active ingredient (F4-A). These formulations had to be applied twice daily to the inside of the forearm. The skin moisture was measured before the start of application and also after 4 weeks. The difference in the corneometer units relative to the starting value was calculated (ΔCU).

The test formulation had the following composition:

Test formulation F4

|  | F4-A | F4-B |
|---|---|---|
| Polyglyceryl-3 methylglucose distearate | 3.0% | 3.0% |
| Glyceryl stearate | 2.0% | 2.0% |
| Stearyl alcohol | 1.0% | 1.0% |
| C12-25 alkyl benzoate | 9.5% | 9.5% |
| PPG-3 myristyl ether | 9.5% | 9.5% |
| Glycerol | 3.0% | 3.0% |
| Phenoxyethanol, methyl paraben, ethyl paraben, butyl paraben, propyl paraben, isobutyl paraben | 0.5% | 0.5% |
| Perfume | 0.1% | 0.1% |
| *Curcuma longa* Dest. | 0% | 0.5% |
| Water | ad 100.0% | ad 100.0% |

Figure 2:
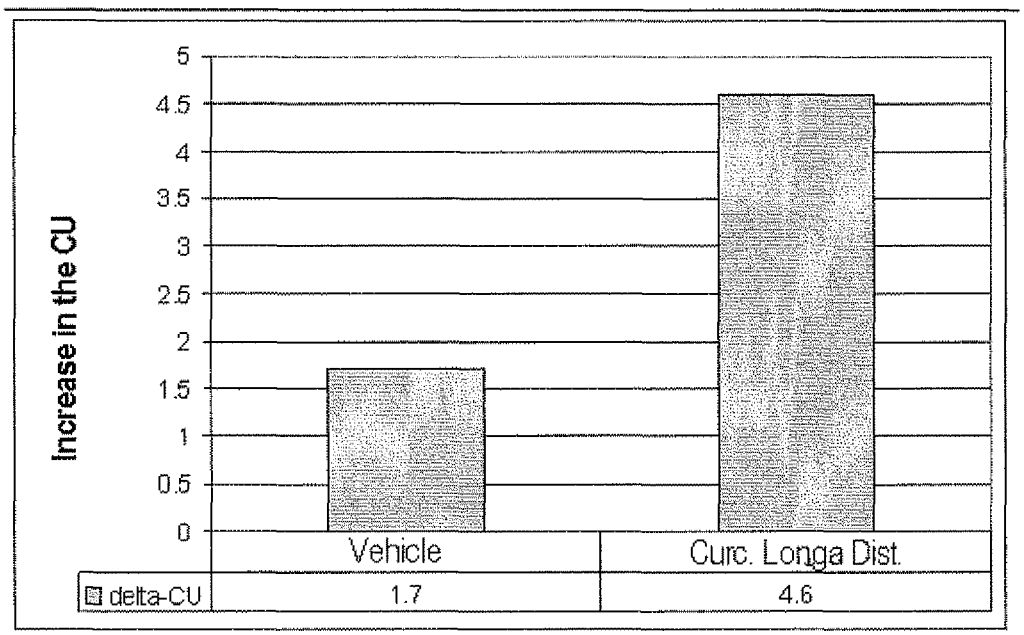
FIG. 2 is a graph illustrating the moisturizing measurements (CU=corneometer units) of a formulation without active ingredient (F4-A) and a formulation with 0.5% of a distilled extract in accordance with the invention (F4-B).

The results of the skin moisture measurements are shown in FIG. 2. (CU=corneometer units)

With the blank formulation (vehicle, F4-A) there was a slight improvement in the skin moisture following application for four weeks. This effect was usual since just, for example, the care effect of the oils present in the formulation leads to slightly increased skin moisture. In contrast to this, in the group who applied a formulation containing 0.5% of the extract according to the invention (F4-B), the skin moisture increased considerably.

Example 6

Influence of the *Curcuma longa* distillate on the skin surface

The characterization of the skin surface was carried out using a special camera, the Visisoscan VC 98 by Courage & Khazaka. This camera had a high-resolution black-white video sensor and a circular UV-A light source for uniform illumination of the skin surface. Using this camera, a greatly magnified image of the skin surface was recorded. Special software was then used to calculate various parameters which describe the condition of the skin surface.

The surface parameter describes the size of the wavy surface of the skin image relative to the level, flattened plane. The less wrinkled the skin surface, thus the lower the measurement.

For the volume parameter, the volume was calculated which would be required to fill the wrinkles with liquid. The more wrinkles present and the deeper these wrinkles, the greater the volume parameter.

Furthermore, the software also calculated so-called texture parameters which also refer to color differences between adjacent pixels. Here, these were the parameters energy, variance, contrast, entropy and homogeneity. In summary, they described the uniformity of the skin surface. An improvement in these parameters signified a more even, more radiant skin image.

An eight-week study with 30 subjects was carried out. The subjects were divided into 2 groups. The first group received the test formulation containing 0.5% of the compound according to the invention (F4-B), the second group received the formulation without active ingredient (F4-A). These formulations had to be applied twice daily to the inside of the forearm. Prior to the start of application and also after 8 weeks, an image of the skin surface was recorded using the camera and evaluated. The percentage difference between the starting value and the 8-week value was then calculated for the various parameters.

Figure 3:
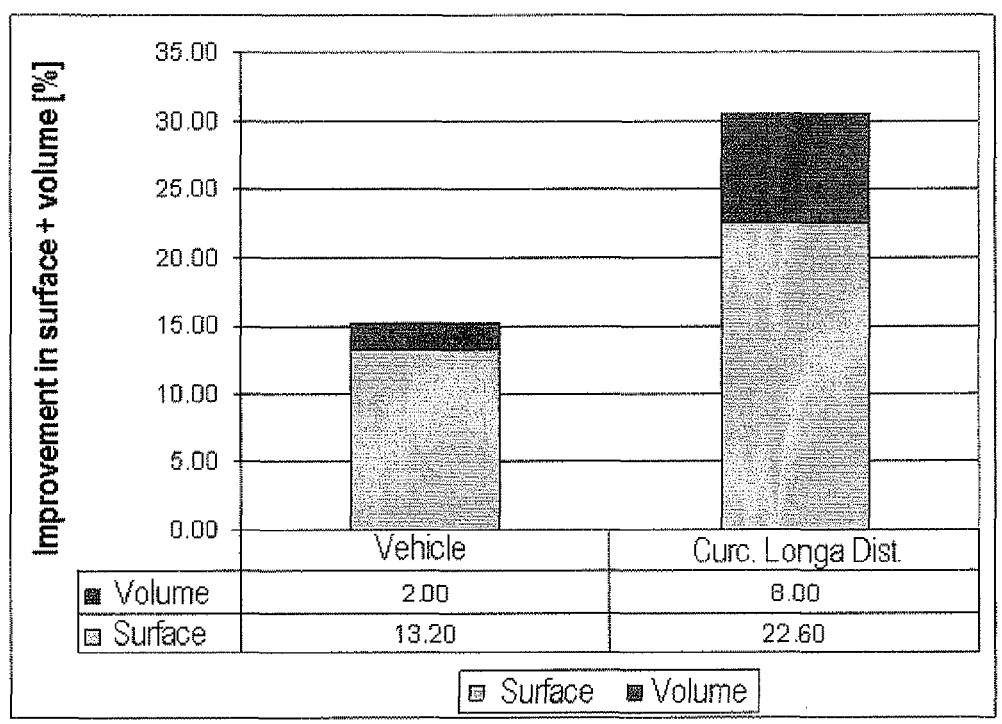
FIG. 3 is a graph showing the surface and volume parameters of formulations F4-A and F4-B.

FIG. 3 gives the improvement in the surface and volume parameters.

Following eight-week application of the blank formulation (F4-A), the only slight improvement already described was again observed. By contrast, the formulation F4-B containing 0.5% of the distilled extract led to a great, significant improvement. The compound according to the invention was consequently able to reduce number of wrinkles and wrinkle depth.

Figure 4:
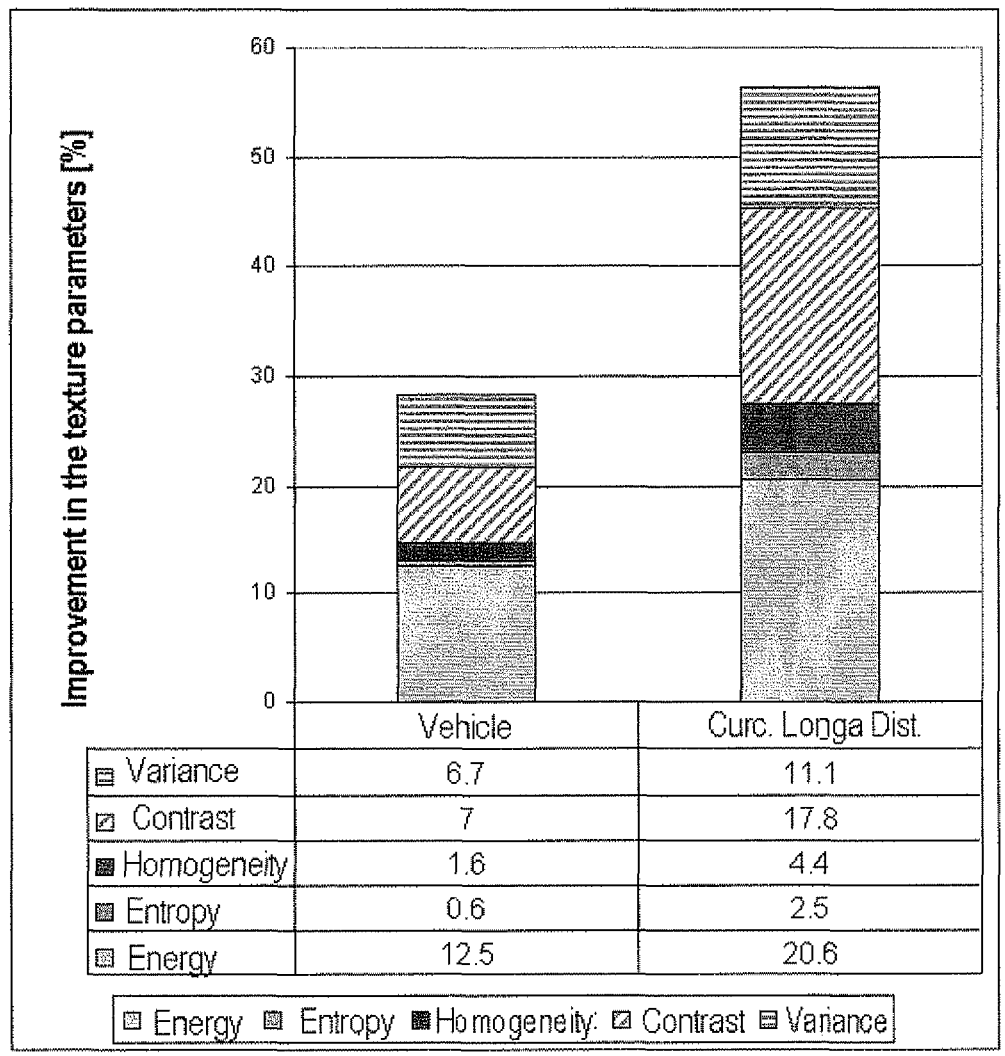
FIG. 4 is a graph showing the percentage change in texture parameter of formulations FA-4 and F4-B.

FIG. 4 shows the percentage change in the texture parameter.

With the blank formulation (F4-A), only a slight improvement in the skin image could be achieved. Following application of the formulation F4-B containing 0.5% of the extract according to the invention, a great improvement in all of the observed parameters was achieved. The distilled *Curcuma longa* extract thus led to a significantly more even, more radiant skin surface.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A method for preparing and using a *Curcuma* extract to provide an even appearance to the skin of a subject in need thereof, the method comprising:
    (i) producing an extract by the following steps: subjecting *Curcuma* rhizomes to supercritical liquid extraction to form a liquid extraction mixture;
    removing solvent present in the liquid extraction mixture to obtain a concentrate; and
    distilling the concentrate at a pressure of less than 1 bar to form said extract as a distillate,
    wherein said extract has a Gardner color number of less than 6; and applying an effective amount of said extract onto the skin of the subject.

2. The process of claim 1, wherein said liquid extraction mixture of *Curcuma* rhizomes is provided by supercritical liquid extraction using a compressed gas as a solvent under supercritical conditions.

3. The process of claim 1, wherein said distilling comprises molecular distillation.

4. The process of claim 1, wherein said distilling comprises falling-film distillation using a pressure of less than 10 mbar.

5. The process of claim 1, wherein said distilling comprises short-path evaporation using a pressure of less than 10 mbar.

6. The process of claim 1, wherein said distilling comprises thin-film distillation using a pressure of less than 10 mbar.

7. The process of claim 1, further comprising separating a curcuminoid-containing solid from said liquid extraction mixture before the solvent removal step, wherein said separating comprises precipitation.

8. The process of claim 7, wherein said liquid extraction mixture of *Curcuma* rhizomes is provided by supercritical liquid extraction using a compressed gas as a solvent under supercritical conditions.

9. The process of claim 7, wherein said distilling comprises molecular distillation.

10. The process of claim 7, wherein said distilling comprises falling-film distillation using a pressure of less than 10 mbar.

11. The process of claim 7, wherein said distilling comprises short-path evaporation using a pressure of less than 10 mbar.

12. The process of claim 7, wherein said distilling comprises thin-film distillation using a pressure of less than 10 mbar.

* * * * *